United States Patent [19]
Wiegand et al.

[11] Patent Number: 5,969,097
[45] Date of Patent: Oct. 19, 1999

[54] HUMAN GUANYLIN

[75] Inventors: Roger C. Wiegand, Chesterfield; Mark G. Currie, St. Charles; Kam Fook Fok, St. Louis, all of Mo.

[73] Assignee: G. D. Searle & Co., Chicago, Ill.

[21] Appl. No.: 07/903,029

[22] Filed: Jun. 23, 1992

[51] Int. Cl.$^6$ .......................... C07K 14/00; C07K 14/435
[52] U.S. Cl. .......................... 530/326; 530/323; 530/300
[58] Field of Search .................... 530/326, 323, 530/300

[56] References Cited

U.S. PATENT DOCUMENTS 5,140,102  8/1992  Currie ........................ 530/326

OTHER PUBLICATIONS

Schultz et al., Cell 63, 941–948 (1990).
Yoshimura et al., FEBS Lett. 181, 138–142 (1985).
Currie et al., Proc. Natl. Acad. Sci, 947–951 It is disclosed that the author is co–inventor.
Glover "Principles of Cloning DNA", *Gene Cloning*, pp. 1–19 1984.

*Primary Examiner*—Frank C. Eisenschenk
*Attorney, Agent, or Firm*—Dennis A. Bennett

[57] ABSTRACT

A novel pentadecapeptide is disclosed which is useful for the control of intestinal fluid absorption and that has the following amino acid sequence

```
Pro-Gly-Thr-Cys-Glu-Ile-Cys-Ala-Tyr-Ala-
1             5                        10

Ala-Cys-Thr-Gly-Cys (SEQ ID NO.1)
           15
```

6 Claims, 7 Drawing Sheets

Fig. 1

```
  1  TCGCTGCCATGAATGCCTTCCTGCTCTTCGCACTGTGCCTCCTTGGGGCCTGGGCCGCCT   60
        MetAsnAlaPheLeuLeu PheAlaLeuCysLeuLeuGlyAlaTrpAlaAlaL
 61  TGGCAGGAGGGGTCACCGTGCAGGATGGAAATTTCTCCTTTTCTCTGGAGTCAGTGAaGA  120
        euAlaGlyGlyValThrValGlnAspGlyAsnPheSerPheSerLeuGluSerValLysL
121  aGCTCAaaGACcTCcAGgAGCcccAGgANCCCAGGGTTGGGAAACTCAGGAACTTTGCAC  180
        ysLeuLysAspLeuGlnGlnProGlnXxxProArgValGlyLysLeuArgAsnPheAlaP
181  CCATCCCTGGTGAACCTGTGGTTCCCATCCTCTGTAGCAACCCGAACTTTCCAGAAGAAC  240
        roIleProGlyGluProValValProIleLeuCysSerAsnProAsnPheProGluGluL
241  TCAAGCCTCTCTGCAAGGAGCCCAATGCCCAGGAGATACTTCAGAGGCTGGAGGAAATCG  300
        euLysProLeuCysLysGluProAsnAlaGlnGluIleLeuGlnArgLeuGluGluIleA
301  CTGAGGACCCGGGCACATGTGAAATCTGTGCCTACGCTGCCTGTACCGGATGCTAGGGGG  360
        laGluAspProGlyThrCysGluIleCysAlaTyrAlaAlaCysThrGlyCysEnd
362  GCTTGCCCACTGCCTGCCTCCCCTCCGCAGCAGGGAAGCTCTTTTCTCCTGCAGTAAGGG  420
421  CCACCCATGATACTCCACTCCCAGCAGCTCAACCTACCCTGGTCCAGTCGGGAGGAGCAG  480
481  CCCGGGGAGGAACTGGGTGACTGGAGGCCTCGCCCCAACACTGTCCTTCCCTGCCACTTC  540
541  AACCCCCAGCTAATAAACCAGATTCCAGAGTAAAAAAAAAAAAAAAAA              589
```

Fig. 2

Gap Weight : 3.000  Average Match : 0.540
Length Weight : 0.100  Average Mismatch : -0.396

Quality : 124.8  Length : 116
Ratio : 1.085  Gaps : 0
Percent Similarity : 73.913  Percent Identity : 65.217

Humpreguan.Pep  x  Ratpreguan.Pep   April 27, 1992  10:29 ..

```
  1 MNAFLLFALCLLGAWAALAGGVTVQDGNFSFSLESVKKLKDLQEPQEPRV  50
    |||:|| .||||||:|.|.:||||||||::||.|||||.||.|.|.| | :
  1 MNAWLLSVLCLLGALAVLVEGVTVQDGDLSFPLESVKQLKHLREVQEPTL  50

51 GKLRNFAPIPGEPVVPILCSNPNFPEELKPLCKEPNAQEILQRLEEIAED 100
    . :.||   ..||.| |||...|||.|:|||..||:|||||||.|:*|
 51 MSHKKFALRLPKPVAPELCSQSAFPEALRPLCEKPNAEEILQRLEAIAQD 100

101 PGTCEICAYAACTGC* 116
    |.||||||||||||||
101 PNTCEICAYAACTGC. 115
```

Activity Comparison of Human and Rat Intestinal Guanylin and STa Enterotoxin.

—○— Sta(13-Mer)
—△— Human Guan
—●— Rat Guanylin

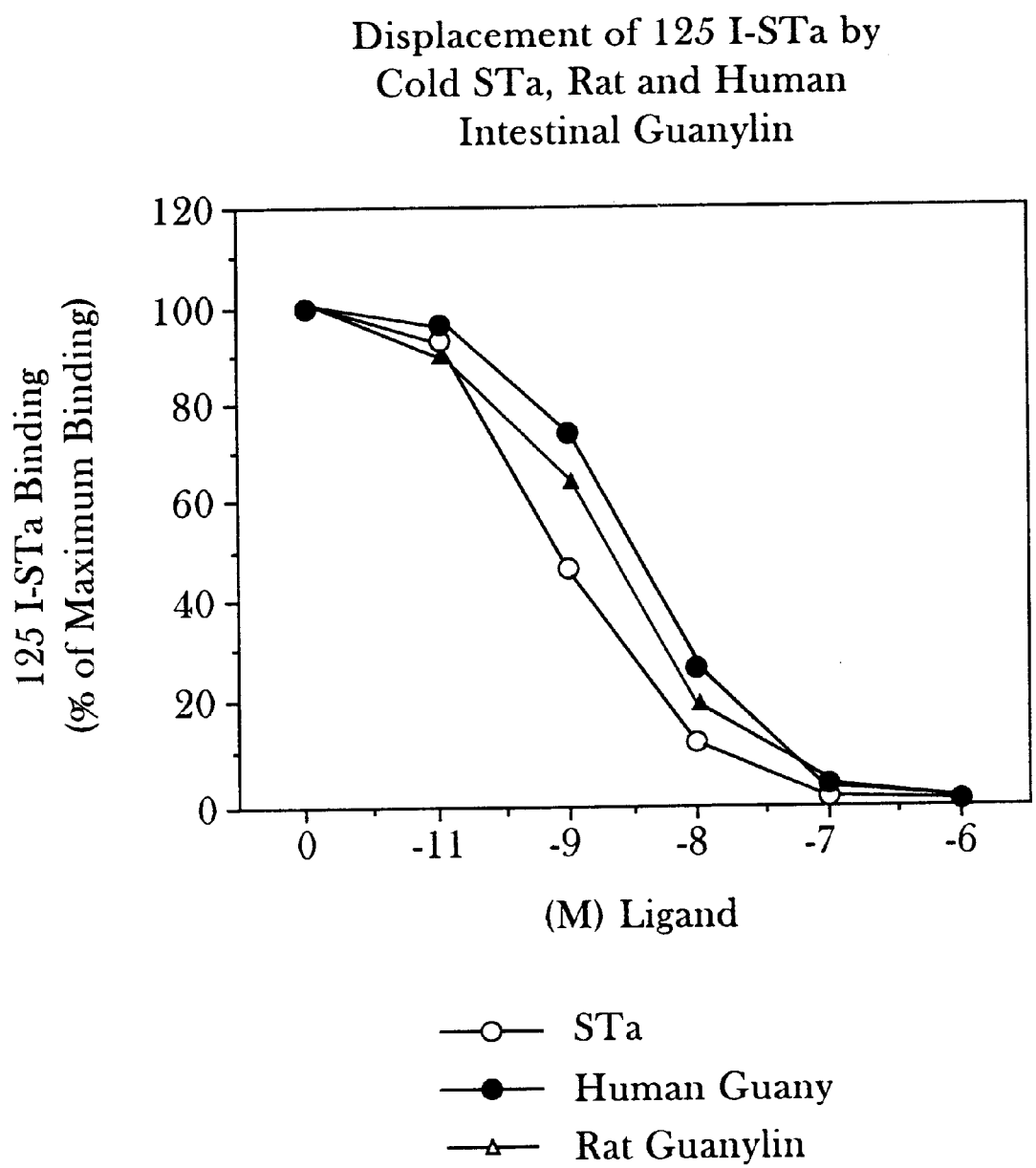

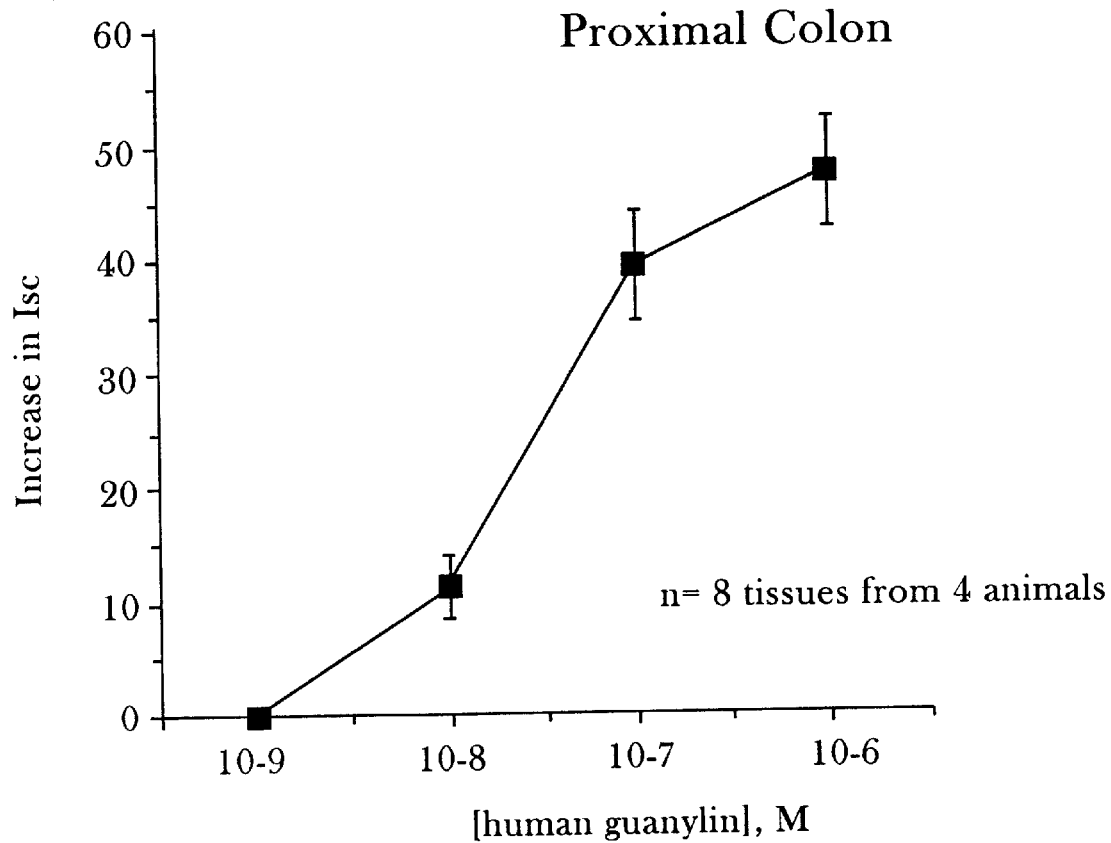

HUMAN GUANYLIN

BACKGROUND OF THE INVENTION

This invention relates to a novel peptide and cDNA which codes for said protein and, more particularly, to human guanylin that is an endogenous regulator of intestinal guanylate cyclase in humans and the cDNA that encodes for said protein.

Guanylate cyclase is composed of a group of proteins that share structural characteristics relative to the enzymatic function of producing cyclic GMP, but differ quite remarkably in their selective activation by ligands. The three major forms of guanylate cyclase are the soluble, particulate, and intestinal (cytoskeletal-associated particulate or STa-sensitive) with each of these forms regulated by different ligands (1,2). Activation of the soluble guanylate cyclase occurs in response to nitric oxide (EDRF), while activation of the particulate enzyme occurs in response to the natriuretic peptides (atrial natriuretic peptide, brain natriuretic peptide, and C-type natriuretic peptide) (1,2). An endogenous activator of the intestinal guanylate cyclase in humans has not previously been identified, however the heat stable enterotoxin from *E. coli* is known to selectively activate this form of the enzyme (3,4). This form of the enzyme is predominantly found in the intestinal epithelial cells with the largest number of receptors oriented towards the lumen (1,2). Recently, the intestinal form of guanylate cyclase has been cloned and expressed from rat small intestinal mucosa (5). This enzyme is characterized by an extracellular receptor binding region, a transmembrane region, an intracellular protein kinase-like region and a cyclase catalytic domain (5).

Pathogenic strains of *E. coli* and other bacteria produce a family of heat stable entertoxins (STs) that activate intestinal guanylate cyclase. STs are acidic peptides 18–19 amino acids in length with six cysteines and three disulfide bridges that are required for full expression of bioactivity (6). The increase of intestinal epithelial cyclic GMP elicited by STs is thought to cause a decrease in water and sodium absorption and an increase in chloride secretion (7, 8). These changes in intestinal fluid and electrolyte transport then act to cause secretory diarrhea. In developing countries, the diarrhea due to STs is the cause of many deaths, particularly in the infant population (9). STs are also considered to be a major cause of traveler's diarrhea in developed countries (10). STs have also been reported to be a leading cause of morbidity in domestic animals (11).

BRIEF DESCRIPTION OF THE INVENTION

In accordance with the present invention a novel pentadecapeptide is provided which has the following amino acid sequence.

```
Pro-Gly-Thr-Cys-Glu-Ile-Cys-Ala-Tyr-Ala-
1             5                  10

Ala-Cys-Thr-Gly-Cys
          15
```

This peptide [Seq. I.D. No. 1], in its oxidized active biologic form has two disulfide bridges, one between cysteine residues at positions 4 and 12 and the other at positions 7 and 15.

DETAILED DESCRIPTION OF THE INVENTION

While the specification concludes with claims particularly pointing out and specifically claiming the subject matter regarded as forming the present invention, it is believed that the invention will be better understood from the following detailed description of preferred embodiments taken in conjunction with the accompanying drawings in which:

FIG. 1 Sequence of the human guanylin cDNA. The sequence is shown with the predicted translation (SEQ ID NO: 4). The guanylin peptide sequence is underlined. [Seq. I.D. No. 2]

FIG. 2 Comparison of rat (SEQ ID NO: 6) and human guanylin (SEQ ID NO: 5) prohormone sequences. This comparison was made with the GCG program using the default settings.

FIG. 3 Bioactivity of human guanylin
  a) Activity in the T84 cell bioassay. As determined by analysis of the effects of the peptides on intracellular cyclic GMP levels.
  b) Competitive inhibition of [$^{125}$I]-STa binding. Unlabeled STa (E), human guanylin (J), or rat guanylin (H) were added in increasing concentrations to a binding assay using [$^{125}$I]-STa as described in Methods.

Figure 4A:
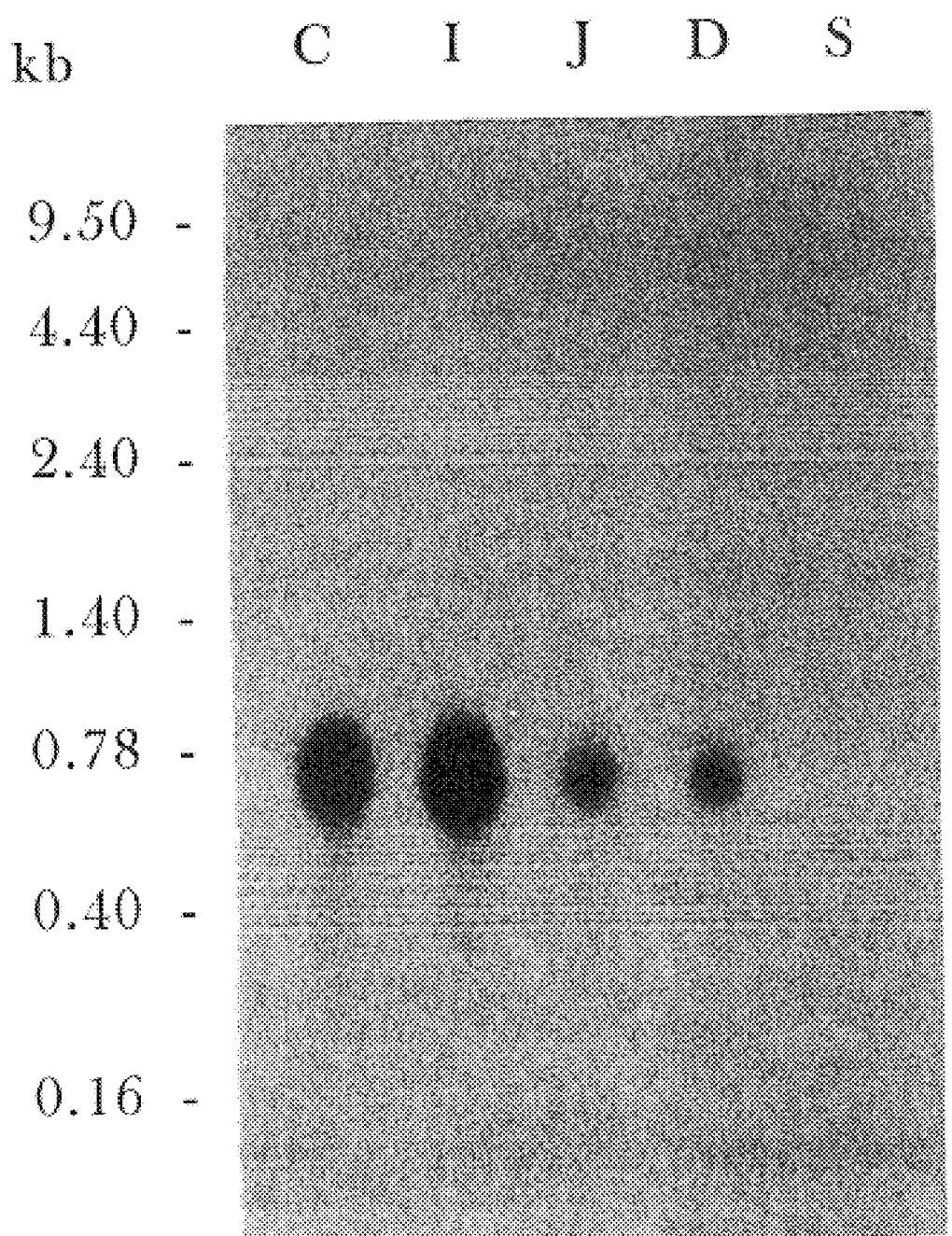
Figure 4B:
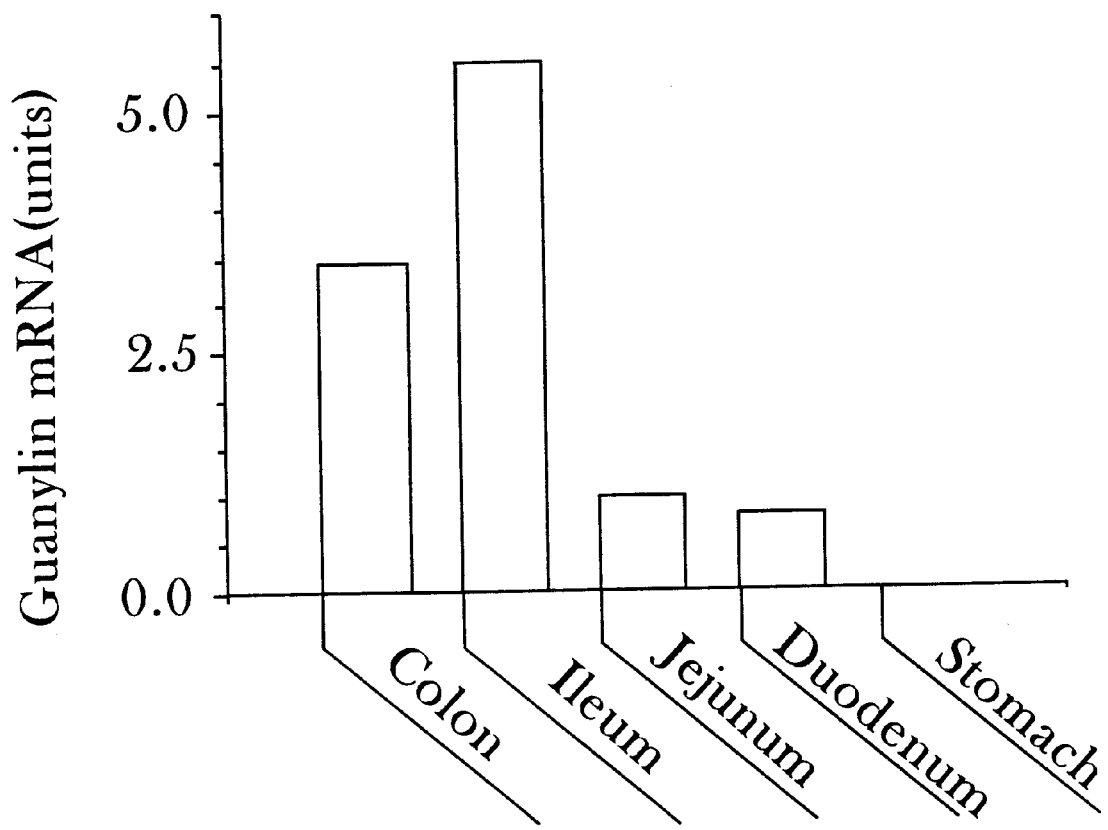

FIG. 4 Northern blot analysis of guanylin steady-state mRNA levels
  a) Cephalocaudal axis of the gut. Ten µg of total RNA isolated from various portions of the human gastrointestinal tract were loaded in each lane. C, colon; I, ilium; J, jejunum; D, duodenum; S, stomach
  b) Tissue distributionas measured by phophoImager TM.

FIG. 5. The effect of guanylin on short circuit current. Cumulative concentration-response curves for the effects of human guanylin on Isc. Human guanylin evoked a concentration-dependent increase and sustained increase in ISC after mucosal addition with EC$_{50}$ of 30 nM. Points and brackets are means∓S.E. for n=8.

In conventional solution phase peptide synthesis, the peptide chain can be prepared by a series of coupling reactions in which the constituent amino acids are added to the growing peptide chain in the desired sequence. The use of various N-protecting groups, e.g., the carbobenzyloxy group or the t-butyloxycarbonyl group (BOC), various coupling reagents, e.g., dicyclohexylcarbodiimide or carbonyldimidazole, various active esters, e.g., esters of N-hydroxyphthalimide or N-hydroxy-succinimide, and the various cleavage reagents, e.g., trifluoroacetic acid (TFA), HCl in dioxane, boron tris-(trifluoracetate) and cyanogen bromide, and reaction in solution with isolation and purification of intermediates is well-known classical peptide methodology.

The preferred peptide synthesis method follows conventional Merrifield solid-phase procedures. See (14). This procedure, though using many of the same chemical reactions and blocking groups of classical peptide synthesis, provides a growing peptide chain anchored by its carboxyl terminus to a solid support, usually cross-linked polystyrene, styrenedivinylbenzene copolymer or, preferably, p-methylbenzhydrylamine polymer for synthesizing peptide amides. This method conveniently simplifies the number of procedural manipulations since removal of the excess reagents at each step is effected simply by washing the polymer.

The acyl group on the N-terminus is conveniently introduced by reaction of an alkanoic anhydride with the peptide on the solid support after deprotection with TFA.

Further background information on the established solid phase synthesis procedure can be had by reference to the treatise by Stewart and Young, "Solid Phase Peptide Synthesis," W. H. Freeman & Co., San Francisco, 1969, and the review chapter by Merrifield in *Advances in Enzymology*, 32, pp. 221–296, F. F. Nold, Ed., Interscience Publishers, New York, 1969; and Erickson and Merrifield, *The Proteins*. 1 Vol. 2, p. 255 et seq. (ed. Neurath and Hill), Academic Press, New York, 1976.

Co-pending application Ser. No. 07/764,461 is hereby incorporated herein by reference in its entirety.

In order to further illustrate the invention, the following exemplary laboratory preparative work was carried out. However, it will be appreciated that the invention is not limited to these examples or the details described therein.

EXAMPLE 1

Materials and Methods

Gene isolation: A human duodenum cDNA library in lgt10 obtained from Clontech (Palo Alto, Calif.) was screened under low stringency hybridization conditions. For screening, 250,000 phages from the library were plated out at 5000 per 88×88 mm square plate and two replica lifts obtained from each plate on nitrocellulose filters. The phage DNA was denatured and fixed to the filter as described Sambrook, J., Fritsch, E. F., and Maniatis, T., Molecular Cloning: a Laboratory Manual. 2nd ed. 1989, Cold Spring Harbor Laboratory Press, Cold Spring Harbor, and the filters were then probed with purified insert from pMON9022, the rat guanylin cDNA in press (13) that had been labeled with $^{32}P$ by random priming to a specific activity of $1\times10^9$ cpm/μg in 20% formamide., 5×SSPE (1×SSPE is 0.15M NaCl, 10 mM NaPO$_4$ 1 mM EDTA, pH 7.4), 2×Denhardts solution (19) 100 μg/ml denatured sonicated calf thymus DNA, 0.1% sodium dodecyl sulfate (SDS) for 16 h at 42° C. After washing twice at 22° C. in 2×SSPE, 0.1% SDS for 15 min, the filters were washed at 50° C. in 1×SSPE, 0.1% SDS for 15 min and then exposed to XAR film overnight at –80° C. with a Quanta III intensifying screen.

Exemplary stringent hybridization conditions would be hybridization of probe (labed to 10^9 cpm/microgram) at 10^6 cpm/ml to 200 ng of target DNA affixed to a nitrocellulose membrane, in 6×SSPE, 0.5% SDS, 50% formamide, 5×Denhardts, 100 ug/ml denatured DNA at 42° C. for 16 h. This would be followed by washing once in 2×SSPE, 0.1% SDS at room temperature and twice for 30 min. each in 0.1×SSPE, 0.5% SDS at 60° C.

Recipes and related methods (gel electrophoresis, blot preparation, etc.) can be found in Sambrook et al., 1989.

mRNA analysis: Adult human intestinal RNAs were obtained as described previously (20). For Northern blots RNA was fractionated by electrophoresis in a 1.7% gel containing formaldehyde, transferred by blotting to a nitrocellulose filter (12) and hybridized with a full-length human guanylin cDNA insert which had been labeled by random priming. Hybridization was performed at 42C. in 50% formamide, 5×SSPE, 0.1% SDS, 200 μg/ml of sonicated denatured salmon sperm DNA, and 1×Denhardts solution. Following washing in 0.2×SSPE at room temperature the filters were autoradiographed for 24 h at –80 C. with a Quantum III intensifying screen. Hybridization was quantitated using a PhosphorImager (Molecular Dynamics, Sunnyvale, Calif.) following a 15 h exposure of the PhosphorImager screen.

Peptide synthesis Human guanylin was synthesized by the solid-phase method (14) with an Applied Biosystems 430A peptide synthesizer on Cyc(4-CH$_2$Bxl)-OCH$_2$-4-(oxymethyl)-phenylacetamidomethyl resin using double coupling program. The following protecting groups for functional groups were used, t-butyloxycarbonyl for α-amino groups; acetamidomethyl for thiol groups of cysteine residues No. 4 and 12, 4-methylbenyl for thiol groups of cysteine residues No. 7 and 15, benzyl for the y-carboxyl of glutamic acid and the hydroxyl group of threonine, bromobenzyl for the phenolic group of tyrosine. Coupling was effected with performed symmetrical anhydride of t-butoxylcarbonylamino acids (Applied Biosystems) or hydroxybenzotriazole ester (for asparagine or glutamine residues), and peptide was deprotected and cleaved from the solid support in hydrogen fluoride, dimethyl sulfide, anisole, and p-thiocresol using 8/1/1/0.5 ratio (v/v/v/w) at 0° C. for 60 min. After removal of hydrogen fluoride and dimethyl sulfide by reduced pressure and anisole and p-thiocresol by extraction with ethyl ether and ethyl acetate sequentially, crude peptides were extracted with a mixture of 0.5M sodium phosphate buffer, pH 8.0 and N,N-dimethylformamide using 1/1 ratio, v/v. After diluted four times with deionized water and the crude peptides were subjected to the first cyclization by dimethyl sulfoxide as described by Tam (15). The monocyclic[Cys(Acm)-4, Cys(Acm)-12] guanylin was purified by reverse-phase chromatography on a 45×300 mm Vydac C18 column using a gradient of 5–40% acetonitrile in 0.05% trifluroacetic acid and then subjected to iodine oxidation in order to cyclize the second pair of cysteine of guanylin. Specifically, purified monocyclic guanylin was dissolved in 50% acetic acid in water and saturated iodine solution in glacial acetic acid was added (1 ml iodine solution per 100 ml on monocyclic guanylic solution). After incubated at room temperature for 2 days in an enclosed glass container, the solution was diluted five-fold with deionized water and extracted with ethyl ether four times for removal of unreacted iodine. After removal of the residual amount of ethyl ether by rotary evaporation the solution of crude product was lyophilized and purified by successive reverse-phase chromatography on a 45×300 mm Vydac C18 column using 5–40% acetonitrile in 0.05% trifluroacetic acid and then on a 19×150 mm μBondapak C18 column, using a 10–30% acetonitrile in 0.05% trifluroacetic acid. The structures and purity of the synthetic peptides were verified by electrospray/mass spectroscopy, amino acid analysis, and gas phase sequence analysis.

(SEQ ID NO:1)

Cell Culture: A cultured human colon carcinoma cell line (T84) was obtained from the American Type Culture Collection (Rockville, Md.) at passage 52. Cells were grown to confluency in 24-well culture plates with a 1:1 mixture of Ham's F12 medium and Dulbecco's modified Eagle's medium (DMEM), supplemented with 10% fetal calf serum, 100 IU/ml penicillin, and 100 μg/ml streptomycin. Cells were used at passages 54–60.

Cyclic GMP determination: Monolayers of T84 cells in 24-well plates were washed twice with 1 ml/well DMEM, then incubated at 37 C. for 10 min with 0.5 ml DMEM containing 1 mM isobutylmethylxanthine (IBMX), a cyclic nucleotide phosphodiesterase inhibitor. Agents and fractions were then added for the indicated time as described in the results section. The media was then aspirated and the reaction terminated by the addition of ice cold 0.5 ml of 0.1N HCl. Aliquots were then evaporated to dryness under nitrogen and then resuspended in 5 mM sodium acetate buffer, pH 6.4. The samples were subsequently measured for cyclic GMP by RIA as described by Steiner et al. (16).

Binding Assay: [$^{125}$I]-STa was prepared by the Iodogen method Fraker, (17). Mf format consistency. T84 cell monolayers in 24-well plates were washed twice with 1 ml of binding buffer (DMEM containing 0.05% bovine serum albumin and 25 mM HEPES, pH 7.2), then incubated for 30 min at 37 C. in 0.5 ml binding buffer with [$^{125}$I]-STa (5–18) (100,000 cpm/well) and various concentrations of guanylin or STa. The cells were then washed 4 times with 1 ml of DMEM and solubilized with 0.5 ml/well 1N NaOH. This volume was transferred to tubes and assayed for radioactivity using a gamma counter. Results are expressed as the percentage specifically bound, each point represents the mean of triplicates.

Results

Relaxed stringency hybridization was used to isolate a human homolog of the rat guanylin gene. A full length rat cDNA fragment was used as a probe to screen a cDNA library made from human duodenum RNA. Thirty-six positives were identified and plaque purified by two subsequent rounds of plating and screening. DNA was prepared from each of these positive clones and analyzed by restriction mapping and Southern blotting. Eleven of the clones remained positive on the Southern blots when probed with the rat guanylin cDNA insert as described above and washed at high stringency. When labeled insert from one of these eleven clones was used to probe all 36 lambda DNA isolates on a Southern blot under high stringency the same eleven clones hybridized. Inserts from four of these clones were subcloned into pGEM7 for sequencing while the end points of the rest were sequenced directly in the lambda DNA. The sequence obtained from these clones is shown in FIG. 1. Most of the clones isolated were artifactual concatenates of unrelated cDNAs, probably selected during the size fractionation step in the construction of the cDNA library due to the small size of the guanylin mRNA. The complete sequence given was found in three non-sibling clones.

The sequence encodes an apparent preprohormone of 115 amino acids. The open reading frame encodes a peptide which shares 14 of 15 amino acids with rat guanylin at its COOH-terminal end. The rat and human cDNAs share about 65–70% identity overall in both the DNA and protein sequences (FIG. 2) and have their major structural features in common. The first 20 residues are hydrophobic, consistent with a leader sequence, there is a polyadenylation signal and poly-A tail at the 3 end of the mRNA. There is one dibasic pair (lys—lys) which might be used for processing, though the location of this sequence is not conserved between rat and human. Production of a 15 amino acid peptide analogous to rat guanylin would result from cleavage between asp and pro at position 100 of the precursor, just as it would in the rat.

To confirm the identity of this gene and assess it's biological activity we synthesized the homolog of the 15 amino acid rat guanylin peptide. Chemical synthesis of the bioactive species in high yield required sequential deprotection and oxidation of the cysteine disulfide pairs to force pairing of cys 4 with cys 12 and cys 7 with cys 15. Air oxidation of a peptide with all four cysteines unprotected gave rise to a mixture of isomers with the correctly folded fraction representing only a small fraction of the total material (data not shown)

Figure 3A:
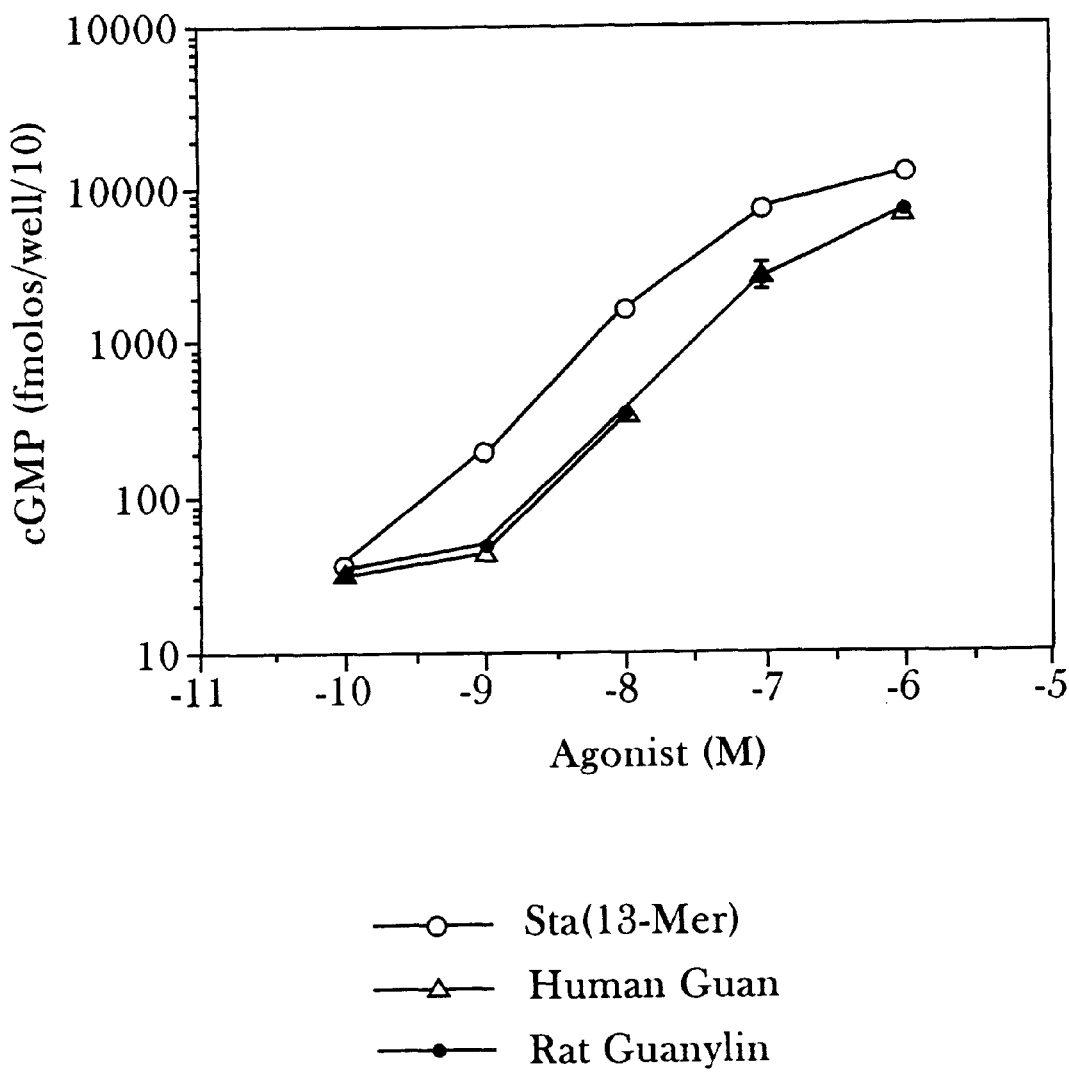

Synthetic human guanylin caused a concentration-dependent increase in T84 cell cyclic GMP (FIG. 3a). Comparison of the activity of human guanylin with rat guanylin indicated that these two peptides possess a similar relative potency to activate intestinal guanylate cyclase. Both human and rat guanylin were about one order of magnitude less potent than STa. A similar profile of relative potency for displacing [$^{125}$I]-STa specific binding from T84 cells was also observed with STa being most potent and human and rat guanylin equipotent (FIG. 3b). Thus, the data indicate that the heat stable enterotoxin is more potent at stimulating intestinal guanylate cyclase than either human or rat guanylin and that all of these peptides share common binding sites.

Northern blot analysis demonstrated that human guanylin, like rat guanylin, is expressed preferentially in the distal regions of the cephalocaudal axis of the gut (FIG. 4a). The highest levels of expression are observed in colon and ileum, lower levels in jejunum and duodenum, and undetectable in stomach. The message was not detected in human kidney mRNA (data not shown).

The major biological actions of guanylin in the intestine are the stimulation of chloride and water secretion and the inhibition of sodium and water absorption. Thus, guanylin should act as a laxative agent for the treatment of constipation. Evidence supporting this proposal is based on the studies cited concerning STa, a structural mimic of guanylin, and data that we have obtained with isolated rat colons. In these experiments, the short circuit current (an indicator of chloride secretion) is measured and the effect of guanylin in increasing concentrations is assessed. The preferred proteins and cDNA encoding therefor have this above mentioned biological actions.

Those skilled in this art will appreciate that minor substitutions can be made to the novel proteins or the cDNA which encodes for them without adversely or detrimentally affecting its biological activity as defined herein and are intended to be within the scope of this invention.

REFERENCES

1. Singh, S. Lowe, K. G., Thorpe, D. S. Rodriquez, H., Kuang, W. -J., Dangott, L. J., Chinkers, M., Goeddel, D. B., and Garbers D. L. (1988) *Nature* 334, 708–712.
2. Waldman, S. A., and Murad, F. (1987) *Pharmacological Reviews* 39, 163–196.
3. Field, M., Graf, L. H., Laird, W. J., and Smith, P. L. (1978) *Proc. Natl. Acad. Sci. USA* 75, 2800–2804.
4. Guerrant, R. L., Hughes, J. M., Chang, B., Robertson, D. C., and Murad, F. (1980) *J. Infect. Dis.* 142, 220–228.
5. Schulz, S., Green, C. K., Yuen, P. S. T., and Garbers, D. L. (1990) *Cell* 63, 941–948.
6. Yoshimura, S., Ikemura, H., Watanabe, H., Aimoto, S., Shimonishi, Y., Hara, S., Takeda, T., Miwatani, T., and Takeda, Y. (1985) *FEBS Letters* 181, 138–142.
7. Field, M., Rao, C. M., and Chang, E.B. (1980) *New England J. Med.* 321, 879–883.
8. Guarino, A., Cohen, M., Thompson, M., Dharmsathaphorn, K., and Giannella, R. (1987) *Am. J. Physiol.* 253, G775–G780.
9. Robins-Browne, R. M. (1987) *Rev. Infect. Dis.* 9, 28–53.
10. Levine, M. M. (1987) *J. Infect. Dis.* 155, 377–389.
11. Burgess, M. N., Bywater, R. J., Cowley, C. M., Mullan, N. A., and Newsome, D. M. *Infect. Immun.* 21, 526–531.
12. Sambrook, J., Fritsch, E. F., and Maniatis, T., Molecular Cloning: a Laboratory Manual. 2nd ed. 1989, Cold Spring Harbor Laboratory Press, Cold Spring Harbor.

13. Wiegand, R. C., Kato, J., and Currie, M. G. (1992) BBRC submitted,
14. Merrifield, R. B. (1963) J. Am. Chem. Soc. 85, 2149–2154.
15. Tam, J. P., Wu, C. -R., Liu, W., and Zhang, J. -W. (1991) J. Am. Chem. Soc. 113, 6657–6662.
16. Steiner, A. L., Paghara, A. S., Chase, L. R., and Kipnis, D. M. (1972) J. Biol. Chem. 247, 1114–1120.
17. Fraker, P. and Speck, J. C. (1978) Biochem. Biophys. Res. Commun. 80, 849–857.
18. Devereux, J., Haeberli, P., and Smithies, O. (1984) Nuc. Acids Rec. 12, 387–395.
19. Denhardt, D. T. (1966) Biochem. Biophys. Res. Commun. 23, 641.
20. Wice, B. M. and Gordon, J. I. (1992) J. Cell. Biol. 116, 405–422.

What is claimed is:

1. An isolated protein consisting essentially of the following amino acid sequence Pro-Gly-Thr-Cys-Glu-Ile-Cys-Ala-Tyr-Ala-
    1              5                  10

Ala-Cys-Thr-Gly-Cys (SEQ ID NO:1).
               15

2. The protein of claim 1 in oxidized form consisting essentially of two disulfide bridges, one between cysteine residues 4 and 12 and the other between cysteine residues 7 and 15.

3. The protein of claim 1 consisting essentially of the amino acid sequence as shown in FIG. 1 (SEQ ID NO.4).

4. An isolated protein consisting of the following amino acid sequence

Pro-Gly-Thr-Cys-Glu-Ile-Cys-Ala-Tyr-Ala-
    1              5                  10

Ala-Cys-Thr-Gly-Cys.
               15

5. The protein of claim 4 in oxidized form consisting of two disulfide bridges, one between cysteine residues 4 and 12 and the other between cysteine residues 7 and 15.

6. The protein of claim 1 consisting of the amino acid sequence as shown in FIG. 1.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
       (A) LENGTH: 15 amino acids
       (B) TYPE: amino acid
       (D) TOPOLOGY: linear (ii) MOLECULE TYPE: peptide (xi) SEQUENCE DESCRIPTION: SEQ ID NO:1:

Pro Gly Thr Cys Glu Ile Cys Ala Tyr Ala Ala Cys Thr Gly Cys
1               5                   10                  15

(2) INFORMATION FOR SEQ ID NO:2:

(i) SEQUENCE CHARACTERISTICS:
       (A) LENGTH: 589 base pairs
       (B) TYPE: nucleic acid
       (C) STRANDEDNESS: double
       (D) TOPOLOGY: linear (ii) MOLECULE TYPE: cDNA (xi) SEQUENCE DESCRIPTION: SEQ ID NO:2:

```
TCGCTGCCAT GAATGCCTTC CTGCTCTTCG CACTGTGCCT CCTTGGGGCC TGGGCCGCCT      60

TGGCAGGAGG GGTCACCGTG CAGGATGGAA ATTTCTCCTT TTCTCTGGAG TCAGTGAAGA     120

AGCTCAAAGA CCTCCAGGAG CCCCAGGANC CAGGGTTGG GAAACTCAGG AACTTTGCAC      180

CCATCCCTGG TGAACCTGTG GTTCCCATCC TCTGTAGCAA CCCGAACTTT CCAGAAGAAC     240

TCAAGCCTCT CTGCAAGGAG CCCAATGCCC AGGAGATACT TCAGAGGCTG GAGGAAATCG     300

CTGAGGACCC GGGCACATGT GAAATCTGTG CCTACGCTGC CTGTACCGGA TGCTAGGGGG     360

GCTTGCCCAC TGCCTGCCTC CCCTCCGCAG CAGGGAAGCT CTTTTCTCCT GCAGTAAGGG     420

CCACCCATGA TACTCCACTC CCAGCAGCTC AACCTACCCT GGTCCAGTCG GGAGGAGCAG     480

CCCGGGGAGG AACTGGGTGA CTGGAGGCCT CGCCCCAACA CTGTCCTTCC CTGCCACTTC     540

AACCCCCAGC TAATAAACCA GATTCCAGAG TAAAAAAAAA AAAAAAAA                  589
```

(2) INFORMATION FOR SEQ ID NO:3:

(i) SEQUENCE CHARACTERISTICS:
       (A) LENGTH: 45 base pairs
       (B) TYPE: nucleic acid
       (C) STRANDEDNESS: double
       (D) TOPOLOGY: linear (ii) MOLECULE TYPE: cDNA (xi) SEQUENCE DESCRIPTION: SEQ ID NO:3:

```
CCGGGCACAT GTGAAATCTG TGCCTACGCT GCCTGTACCG GATGC                      45
```

(2) INFORMATION FOR SEQ ID NO:4:

(i) SEQUENCE CHARACTERISTICS:
        (A) LENGTH: 115 amino acids
        (B) TYPE: amino acid
        (D) TOPOLOGY: linear (ii) MOLECULE TYPE: protein (xi) SEQUENCE DESCRIPTION: SEQ ID NO:4:

```
Met Asn Ala Phe Leu Leu Phe Ala Leu Cys Leu Leu Gly Ala Trp Ala
1               5                   10                  15

Ala Leu Ala Gly Gly Val Thr Val Gln Asp Gly Asn Phe Ser Phe Ser
            20                  25                  30

Leu Glu Ser Val Lys Lys Leu Lys Asp Leu Gln Glu Pro Gln Xaa Pro
        35                  40                  45

Arg Val Gly Lys Leu Arg Asn Phe Ala Pro Ile Pro Gly Glu Pro Val
    50                  55                  60

Val Pro Ile Leu Cys Ser Asn Pro Asn Phe Pro Glu Glu Leu Lys Pro
65                  70                  75                  80

Leu Cys Lys Glu Pro Asn Ala Gln Glu Ile Leu Gln Arg Leu Glu Glu
                85                  90                  95

Ile Ala Glu Asp Pro Gly Thr Cys Glu Ile Cys Ala Tyr Ala Ala Cys
            100                 105                 110

Thr Gly Cys
        115
```

(2) INFORMATION FOR SEQ ID NO:5:

(i) SEQUENCE CHARACTERISTICS:
        (A) LENGTH: 115 amino acids
        (B) TYPE: amino acid
        (D) TOPOLOGY: linear (ii) MOLECULE TYPE: peptide (xi) SEQUENCE DESCRIPTION: SEQ ID NO:5:

```
Met Asn Ala Phe Leu Leu Phe Ala Leu Cys Leu Leu Gly Ala Trp Ala
1               5                   10                  15

Ala Leu Ala Gly Gly Val Thr Val Gln Asp Gly Asn Phe Ser Phe Ser
            20                  25                  30

Leu Glu Ser Val Lys Lys Leu Lys Asp Leu Gln Glu Pro Gln Glu Pro
        35                  40                  45

Arg Val Gly Lys Leu Arg Asn Phe Ala Pro Ile Pro Gly Glu Pro Val
    50                  55                  60

Val Pro Ile Leu Cys Ser Asn Pro Asn Phe Pro Glu Glu Leu Lys Pro
65                  70                  75                  80

Leu Cys Lys Glu Pro Asn Ala Gln Glu Ile Leu Gln Arg Leu Glu Glu
                85                  90                  95

Ile Ala Glu Asp Pro Gly Thr Cys Glu Ile Cys Ala Tyr Ala Ala Cys
            100                 105                 110

Thr Gly Cys
        115
```

(2) INFORMATION FOR SEQ ID NO:6:

(i) SEQUENCE CHARACTERISTICS:
        (A) LENGTH: 115 amino acids
        (B) TYPE: amino acid
        (D) TOPOLOGY: linear

```
    (ii) MOLECULE TYPE: peptide (xi) SEQUENCE DESCRIPTION: SEQ ID NO:6:

Met Asn Ala Trp Leu Leu Ser Val Leu Cys Leu Leu Gly Ala Leu Ala
1               5                   10                  15

Val Leu Val Glu Gly Val Thr Val Gln Asp Gly Asp Leu Ser Phe Pro
            20                  25                  30

Leu Glu Ser Val Lys Gln Leu Lys His Leu Arg Glu Val Gln Glu Pro
        35                  40                  45

Thr Leu Met Ser His Lys Lys Phe Ala Leu Arg Leu Pro Lys Pro Val
    50                  55                  60

Ala Pro Glu Leu Cys Ser Gln Ser Ala Phe Pro Glu Ala Leu Arg Pro
65              70                  75                  80

Leu Cys Glu Lys Pro Asn Ala Glu Glu Ile Leu Gln Arg Leu Glu Ala
            85                  90                  95

Ile Ala Gln Asp Pro Asn Thr Cys Glu Ile Cys Ala Tyr Ala Ala Cys
            100                 105                 110

Thr Gly Cys
        115
```